United States Patent
Watanabe et al.

(10) Patent No.: US 10,959,920 B2
(45) Date of Patent: Mar. 30, 2021

(54) OIL-IN-WATER TYPE EMULSION COSMETIC

(71) Applicant: SHISEIDO COMPANY, LTD., Tokyo (JP)

(72) Inventors: Tsukasa Watanabe, Yokohama (JP); Kahori Ishida, Yokohama (JP); Takahiro Katori, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/649,302

(22) PCT Filed: Sep. 3, 2018

(86) PCT No.: PCT/JP2018/032604
§ 371 (c)(1),
(2) Date: Mar. 20, 2020

(87) PCT Pub. No.: WO2019/065104
PCT Pub. Date: Apr. 4, 2019

(65) Prior Publication Data
US 2020/0261331 A1    Aug. 20, 2020

(30) Foreign Application Priority Data

Sep. 29, 2017   (JP) .............................. JP2017-191700

(51) Int. Cl.
| | | |
|---|---|---|
| *A61K 8/06* | (2006.01) | |
| *A61K 8/9706* | (2017.01) | |
| *A61K 8/02* | (2006.01) | |
| *A61K 8/04* | (2006.01) | |
| *A61K 8/25* | (2006.01) | |
| *A61K 8/37* | (2006.01) | |
| *A61K 8/81* | (2006.01) | |
| *A61K 8/86* | (2006.01) | |
| *A61Q 1/00* | (2006.01) | |
| *A61Q 5/00* | (2006.01) | |
| *A61Q 17/04* | (2006.01) | |

(52) U.S. Cl.
CPC .............. *A61K 8/062* (2013.01); *A61K 8/022* (2013.01); *A61K 8/025* (2013.01); *A61K 8/042* (2013.01); *A61K 8/25* (2013.01); *A61K 8/37* (2013.01); *A61K 8/8152* (2013.01); *A61K 8/86* (2013.01); *A61K 8/9706* (2017.08); *A61Q 1/00* (2013.01); *A61Q 5/00* (2013.01); *A61Q 17/04* (2013.01); *A61K 2800/592* (2013.01)

(58) Field of Classification Search
None
See application file for complete search history.

(56) References Cited

U.S. PATENT DOCUMENTS 9,289,498 B2 * 3/2016 Matsuo .................... A61K 8/73

FOREIGN PATENT DOCUMENTS

| JP | 2001-342451 | 1/2001 |
|---|---|---|
| JP | 2008-303163 | 12/2008 |
| JP | 2009-203200 | 9/2009 |
| JP | 2009-286748 | 10/2009 |
| JP | 2011-051922 | 3/2011 |
| JP | 2011-073971 | 4/2011 |
| JP | 2011-074071 | 4/2011 |
| JP | 2011-111446 | 6/2011 |
| JP | 2011-236202 | 11/2011 |
| JP | 2012-087084 | 5/2012 |
| JP | 2012-201664 | 10/2012 |
| JP | 2014-210770 | 11/2014 |

OTHER PUBLICATIONS

PCT/JP2018/032604, International Search Report (ISR) and Written Opinion (WO), dated Nov. 27, 2018, 7 pages—English, 7 pages—Japanese.

* cited by examiner

*Primary Examiner* — Nannette Holloman
(74) *Attorney, Agent, or Firm* — Andrew F. Young, Esq.; Nolte Lackenbach Siegel

(57) ABSTRACT

An oil-in-water type emulsion cosmetic exhibits a high-level sunscreen effect and has a low viscosity and a high stability and is easy to use. The oil-in-water type emulsion cosmetic includes (A) an agar microgel, (B) one or more kinds of powders selected from (b1) a clay mineral powder and (b2) a highly oil-absorbing spherical powder, (C) a polyoxyethylene-hardened castor oil having an HLB value of 10-17; (D) an oil-soluble UV absorber, (E) 0.01-0.13 mass % of an (acrylate/alkyl acrylate ($C_{10-30}$)) cross polymer, and (F) 0-0.5 mass % of a UV scattering agent, and is characterized in that the viscosity at 25° C. is not higher than 10,000 mPa·s.

4 Claims, No Drawings

OIL-IN-WATER TYPE EMULSION COSMETIC

CROSS REFERENCE TO RELATED APPLICATIONS

This application relates to and claims priority as a § 371 national phase, from PCT/JP2018/032604 filed Sep. 3, 2018, the entire contents of which are incorporated herein by reference, which in turn claims priority from JP 2017-191700 filed Sep. 29, 2017.

FIGURE SELECTED FOR PUBLICATION

None

TECHNICAL FIELD

The present invention relates to an oil-in-water emulsion cosmetic. More specifically, the present invention provides an oil-in-water emulsion cosmetic that has an excellent texture, that has low viscosity and that is stable, while also having high sunscreen effects. The oil-in-water emulsion cosmetic of the present invention can be applied to sunscreen cosmetics as a matter of course, but also has the potential to be widely applied to makeup products, hair-care products and the like.

BACKGROUND ART

The ultraviolet absorbing agents that are blended into sunscreen cosmetics can be largely divided between oil-soluble ultraviolet absorbing agents and water-soluble ultraviolet absorbing agents.

Water-soluble ultraviolet absorbing agents can impart a watery feeling in use to sunscreen cosmetics, but it is difficult to achieve sufficient ultraviolet protection performance in comparison to oil-soluble ultraviolet absorbing agents.

On the other hand, although oil-soluble ultraviolet absorbing agents have excellent ultraviolet protection performance, when used in an amount sufficient to achieve high sunscreen effects, the oil content becomes too high and the cosmetic becomes unstable. Additionally, the feeling in use becomes oily and wateriness becomes deficient.

As an attempt to obtain a sunscreen cosmetic having high ultraviolet protection performance while also having a watery feeling in use, there has been a proposal to use a water-soluble ultraviolet absorbing agent as a sunscreen agent, and to blend in an agar microgel in order to amplify the ultraviolet protection performance thereof (Patent Document 1). Microgels of this type are also widely known for use as thickeners since they lack stickiness and squeakiness, and have an excellent texture (Patent Document 2).

However, even when an amplifying agent such as an agar microgel is used, it is difficult to realize high sunscreen effects, for example, of SPF 50+, with cosmetics using a water-soluble ultraviolet absorbing agent as the base.

Therefore, as a means for simultaneously obtaining both high ultraviolet protection performance and feeling in use, it is possible to contemplate using an oil-soluble ultraviolet absorbing agent as a main agent in a sunscreen agent, suppressing the content thereof as much as possible, and improving the ultraviolet protection performance with an amplifying agent such as an agar microgel.

However, when an oil-soluble ultraviolet absorbing agent is combined with an amplifying agent such as an agar microgel, the oil content becomes high and the stability of the cosmetic is lost. Additionally, when the cosmetic is applied, there is an oily and sticky feeling in use.

RELATED ART

Patent Documents

Patent Document 1: JP 2011-051922 A
Patent Document 2: JP 2001-342451 A

SUMMARY OF THE INVENTION

Problem to be Solved by the Invention

The present invention provides an oil-in-water emulsion cosmetic that has an excellent texture, that has low viscosity and that is stable, while also having high-level sunscreen effects (an ultraviolet protection performance value (absorbance integral value) of 95 or higher).

Means for Solving the Problem

The present invention provides an oil-in-water emulsion cosmetic having a viscosity, at 25° C., of 10000 mPa·s or lower, and containing:
(A) an agar microgel;
(B) one or more powders selected from among (b1) clay mineral powders and (b2) highly oil-absorbent spherical powders;
(C) a polyoxyethylene-hardened castor oil having an HLB value of 10 to 17;
(D) an oil-soluble ultraviolet absorbing agent;
(E) 0.01% to 0.13% by mass of an (acrylates/($C_{10-30}$) alkyl acrylate) crosspolymer; and
(F) 0% to 0.5% by mass of an ultraviolet scattering agent.

Effects of the Invention

The present invention can obtain excellent stability, low viscosity and a smooth feeling when applied, while also realizing high-level sunscreen effects, by blending an agar microgel, a specific powder, a polyoxyethylene-hardened castor oil and a specific amount of an (acrylates/($C_{10-30}$) alkyl acrylate) crosspolymer into an oil-in-water emulsion cosmetic containing an oil-soluble ultraviolet absorbing agent as the main agent in a sunscreen agent. Specifically, by blending an oil-soluble ultraviolet absorbing agent with various components that amplify the effects thereof, high sunscreen effects can be achieved with a smaller amount of oil-soluble ultraviolet absorbing agents than in conventional cosmetics. Additionally, since high-level sunscreen effects can be achieved, there is no need to blend in an especially high amount of ultraviolet scattering agents, and there is no tendency for whitening to occur after application. Furthermore, by blending a polyoxyethylene-hardened castor oil and an (acrylates/($C_{10-30}$) alkyl acrylate) crosspolymer while being able to reduce the oil-soluble ultraviolet absorbing agent content at the same time, it is possible to impart a smooth feeling in use at the time of application while also providing low viscosity and excellent stability.

MODES FOR CARRYING OUT THE INVENTION

Hereinafter, the present invention will be explained in detail.

<(A) Agar Microgel>

In the present invention, the (A) agar microgel refers to agar that is dissolved in water or an aqueous component, allowed to cool, and gelled, then atomized to form a microgel.

The agar is not particularly restricted as long as it contains agarose, which has high gelling power, as the main component, and natural substances or commercial products may be used as is. The agar concentration in the agar microgel is preferably 0.01% to 1.5% by mass, and more preferably 0.05% to 1% by mass.

The aqueous component is not particularly limited as long as it is an aqueous component that is used in the cosmetic and pharmaceutical fields. For example, it is possible to add a glycol such as 1,3-butylene glycol or propylene glycol, or a lower alcohol such as ethanol or propanol, as well as components that are generally blended as water-phase components in cosmetics. Specifically, examples include, but are not limited to, chelating agents such as metaphosphates and edetates, pH adjusting agents, preservatives and the like.

The agar microgel may be obtained in accordance with a conventional method, and for example, may be produced by means of the method disclosed in JP 2001-342451 A. In the present invention, the average particle size of the agar microgel is 0.1 to 1000 μm, preferably approximately 1 to 300 μm, and more preferably approximately 10 to 200 μm. Additionally, the gel strength of the agar microgel is not particularly limited as long as it is of a level such that the gel itself is able to maintain its shape.

In the present invention, the blended amount of the (A) agar microgel in the oil-in-water emulsion cosmetic is preferably 10% to 40% by mass, and more preferably 15% to 30% by mass, relative to the total mass of the oil-in-water emulsion cosmetic.

<(B) Powder>

The (B) powder used in the present invention is generally blended for the purpose of improving the feeling in use in a normal cosmetic, but in the present invention, has the effect of amplifying the ultraviolet protection performance of the (D) oil-soluble ultraviolet absorbing agent, like the above-mentioned (A) agar microgel.

As the powder, it is possible to use one or more powders selected from among (b1) clay mineral powders and (b2) highly oil-absorbent spherical powders.

(b1) Clay Mineral Powder

As clay mineral powders, it is possible to use both natural and synthetic types. Specifically, talc (hydrated magnesium silicate: $3MgO \cdot 4SiO_2 \cdot H_2O$), kaolin (hydrated aluminum silicate: $Al_2O_3 \cdot 2SiO_2 \cdot 2H_2O$), saponite (hydrated aluminum magnesium silicate: mixture of $SiO_2$, $Al_2O_3$, MgO and water), sericite (microcrystalline hydrated aluminum potassium silicate: $K_2O \cdot 3Al_2O_3 \cdot 6SiO_2$, $2H_2O$), mica (hydrated aluminum potassium silicate: $KAl_2 \cdot AlSi_3O_{10}(OH)_2$), boron nitride (BN) and the like are preferably used. Among these, talc is particularly preferred.

(b2) Highly Oil-Absorbent Spherical Powder

The highly oil-absorbent spherical powder refers to a spherical powder having an oil absorption rate, as measured under the JIS K5101-13-2 standard, of 20 ml/100 g or higher, and more preferably 40 ml/100 g or higher.

As the specific measurement procedure for the oil absorption rate, 5 g of the powder is taken onto a glass plate, first-grade linseed oil is dripped thereon, the amount of first-grade linseed oil that is necessary for the powder to form a single lump while kneading the powder with a spatula is determined, and this amount, converted to the amount per 100 g of the powder, is defined as the oil absorption rate of the powder. In other words, the oil absorption rate (ml/100 g) is determined by the following formula:

$$O = (V/m) \times 100$$

In this formula, O represents the oil absorption rate (ml/100 g), m represents the mass (g) of the powder, and V represents the volume (ml) of the first-grade linseed oil that has been consumed.

Specific examples of highly oil-absorbent spherical powders include, but are not limited to, silicic anhydride (oil absorption rate 20 ml/100 g, 120 ml/100 g, etc.), poly(methyl methacrylate) (oil absorption rate 46.5 ml/100 g), cellulose acetate spherical powders (oil absorption rate 70 ml/100 g) and the like. It is possible to use commercial products, examples of which include Sunsphere® L51S (manufactured by AGC Si-Tech), Techpolymer® AQUA (manufactured by Sekisui Plastics), Celluloflow (manufactured by Chisso Corporation) and the like.

In the present invention, the blended amount of the (B) powder in the oil-in-water emulsion cosmetic is preferably 1% to 10% by mass, and more preferably 2% to 8% by mass, relative to the total mass of the oil-in-water emulsion cosmetic.

<(C) Polyoxyethylene-Hardened Castor Oil>

The (C) polyoxyethylene-hardened castor oil that can be used in the present invention is preferably of one or more types selected from among those having an HLB value of 10 to 17, and more preferably those having an HLB value of 12 to 15. Among these, a particularly preferable example is POE (60) hardened castor oil (HLB=14.0). As commercial products, it is possible to use Nikkol® HCO-60 (manufactured by Nikko Chemicals) and the like.

In the present invention, the blended amount of the (C) polyoxyethylene-hardened castor oil in the oil-in-water emulsion cosmetic is preferably 0.1% to 1% by mass, and more preferably 0.2% to 0.8% by mass, relative to the total mass of the oil-in-water emulsion cosmetic.

<(D) Oil-Soluble Ultraviolet Absorbing Agent>

The (D) oil-soluble ultraviolet absorbing agent in the present invention may be of a type that is conventionally used in cosmetics, and is not particularly limited. Examples include methoxycinnamic acid derivatives, salicylic acid derivatives, benzoyl derivatives, camphor derivatives, para-aminobenzoic acid derivatives, triazine derivatives, benzophenone derivatives and polysilicones. Specific examples include 2-ethylhexyl para-methoxycinnamate, oxybenzone, 4-t-butyl-4'-methoxydibenzoylmethane, octyl triazone, bis-ethylhexyloxyphenol methoxyphenyl triazine, dioctyl butamido triazone, diethylamino hydroxybenzoyl hexyl benzoate, 2-cyano-3,3-diphenylacrylic acid-2'-ethylhexyl ester, polysilicone-15, octyl salicylate, homomenthyl salicylate, p-methylbenzylidene camphor and the like. These may be blended as one type or as a combination of two or more types as needed.

In the present invention, the blended amount of the (D) oil-soluble ultraviolet absorbing agent in the oil-in-water emulsion cosmetic is preferably 5% to 20% by mass, and more preferably 10% to 18% by mass, relative to the total mass of the oil-in-water emulsion cosmetic.

<(E) (Acrylates/($C_{10-30}$) Alkyl Acrylate) Crosspolymer>

The (E) (acrylates/($C_{10-30}$) alkyl acrylate) crosspolymer used in the present invention is a polymer obtained by esterizing, by means of an alkyl group, at least some of the carboxyl groups in a polymer having acrylic acid and/or methacrylic acid as the main chain. The alkyl group bonded by means of an ester bond may be linear or branched, and has 10 to 30 carbon atoms. Examples of commercial products that can serve as the polymer include PEMULEN® TR-1, TR-2 (both manufactured by The Lubrizol Corporation) and the like.

In the present invention, the blended amount of the (E) (acrylates/($C_{10-30}$) alkyl acrylate) crosspolymer in the oil-in-water emulsion cosmetic is preferably 0.01% to 0.13% by mass, and more preferably 0.05% to 0.12% by mass, relative to the total mass of the oil-in-water emulsion cosmetic.

<(F) Ultraviolet Scattering Agent>

In the present invention, it is possible to optionally blend in an (F) ultraviolet scattering agent in order to further improve the ultraviolet protection performance. However, even when blended in, the amount should be 0.5 mass % or less relative to the total weight of the oil-in-water emulsion cosmetic. By setting the amount of the ultraviolet scattering agent to be within the range 0% to 0.5% by mass, it is possible to suppress whitening after application.

Specific examples of the ultraviolet scattering agent include titanium dioxide, chromium oxide, iron oxide, zinc oxide, barium sulfate and the like. Additionally, these may be subjected to a surface hydrophobic treatment, examples of the surface treatment includes silicone treatments such as those using methyl hydrogen polysiloxane, methyl polysiloxane and the like; alkyl silane treatments; fluorine treatments such as those using perfluoroalkyl phosphoric acid esters and perfluoroalcohols; and amino acid treatments such as those using N-acylglutamic acid; as well as lecithin treatments; metal soap treatments; fatty acid treatments; alkyl phosphoric acid ester treatments and the like.

The ultraviolet scattering agent preferably has an average primary particle size of 100 nm or smaller, and more preferably 80 nm or smaller. If the average primary particle size is greater than 100 nm, then there is a tendency for this to be a cause of whitening or white residues. In the present invention, the average primary particle size is a value determined, for example, as the arithmetic mean of the long axes and the short axes of the particles based on transmission electron microscope photographs.

The blended amount of the (F) ultraviolet scattering agent in the present invention, as mentioned above, is at most 0.5% by mass or less, preferably 0.3% by mass or less, and more preferably 0.1% by mass or less, relative to the total mass of the oil-in-water emulsion cosmetic. If more than 0.5% by mass is blended, then the whiteness after application becomes conspicuous, and in some cases, there is a powdery feeling in use.

<Viscosity>

The oil-in-water emulsion cosmetic of the present invention has a viscosity, at 25° C., of 10000 mPa·s or lower, preferably 9000 mPa·s or lower, and more preferably 8000 mPa·s or lower. In the present invention, the "viscosity" is a value measured by a B-type viscometer at 25° C.

Aside from the above-mentioned components, it is possible to appropriately blend into the oil-in-water emulsion cosmetic of the present invention, as needed, other optional additive components that are normally used in external skin preparations such as cosmetic products and pharmaceutical products, within a range not compromising the purpose and the effects of the present invention. Examples include, but are not limited to, oils and fats, waxes, hydrocarbon oils, higher fatty acids, higher alcohols, synthetic ester oils, silicone oils, oil-phase thickeners, surfactants, water-soluble ultraviolet absorbing agents, chelating agents, lower alcohols, polyhydric alcohols, pH adjusters, antioxidants, powder components, fragrances, water and the like.

By blending, for example, an oil-phase thickener as an optional additive component in the oil-in-water emulsion cosmetic of the present invention, it is possible to further improve the stability and the texture by adjusting the viscosity of the oil phase.

As the oil-phase thickener, it is particularly preferable to use, for example, a dextrin fatty acid ester. The dextrin fatty acid ester can be used without any particular restrictions as long as it is an ester of dextrin or reduced dextrin with a higher fatty acid, and is generally used in cosmetics. As the dextrin or reduced dextrin, it is preferable to use one having an average degree of sugar polymerization of 3 to 100. Additionally, as the fatty acid forming the dextrin fatty acid ester, it is preferable to use a saturated fatty acid having 8 to 22 carbon atoms. Specific examples include dextrin palmitate, dextrin oleate, dextrin stearate, dextrin myristate, dextrin (palmitate/2-ethylhexanoate) and the like. Preferable examples of commercial products include Rheopearl® TT (manufactured by Chiba Flour Milling).

When blending an oil-phase thickener into the oil-in-water emulsion cosmetic of the present invention, the blended amount thereof should preferably be 0.1% to 5% by mass, more preferably 0.2% to 2% by mass, and more preferably 0.4% to 1% by mass, relative to the total mass of the oil-in-water emulsion cosmetic.

Additionally, by blending a humectant as an optional additive component in the oil-in-water emulsion cosmetic of the present invention, it is possible to further improve the texture by raising the moisturizing effects.

The humectant is not particularly limited as long as it is conventionally used in cosmetic products. Specific examples include polyhydric alcohols such as glycerin (for example, dynamite glycerin), propylene glycol, 1,3-butylene glycol and sorbitol, mucosaccharides such as hyaluronic acid and chondroitin sulfate, natural moisturizing factors (NMF) or analogs thereof such as amino acids, pyrrolidone carboxylic acid (PCA) and lactic acid, intercellular lipids or analogs thereof, vegetable extracts, protein lysates such as soluble collagen, elastin and keratin, chitin, chitosan, yeast extracts, seaweed extracts and the like.

When blending a humectant into the oil-in-water emulsion cosmetic of the present invention, the blended amount thereof should be 1% to 20% by mass, and more preferably 5% to 20% by mass.

Furthermore, by blending in a polymeric emulsifier such as carboxyvinyl polymer or xanthan gum as an optional additive component, it is possible to further improve the watery texture and the preparation stability. Even among polymeric emulsifiers, carboxyvinyl polymers are particularly preferred.

Carboxyvinyl polymers (carbomers) are water-soluble vinyl polymers having carboxyl groups, and are specifically polymers having acrylic acid and/or methacrylic acid as the main chains. As commercial products that are carboxyvinyl polymers, it is possible to use Carbopol® 940, Carbopol 941, Carbopol® 980, Carbopol® 981 (all manufactured by The Lubrizol Corporation) or the like.

When blending a carboxyvinyl polymer into the oil-in-water emulsion cosmetic of the present invention, the blended amount thereof should be 0.001% to 0.1% by mass, and more preferably 0.005% to 0.05% by mass.

Additionally, the oil-in-water emulsion cosmetic of the present invention has sufficient stability by having the above-described features, but the stability can be further improved by blending in an amphoteric surfactant as an optional additive component.

Examples of amphoteric surfactants include alkyl betaine-type amphoteric surfactants, amido betaine-type amphoteric surfactants, imidazolinium betaine-type amphoteric surfactants, sulfobetaine-type amphoteric surfactants and the like. Particularly preferable amphoteric surfactants include lauryl betaine (Nissan Anon BL-SF, manufactured by NOF Corporation), cocamidopropyl betaine (Lebon 2000HG, manufactured by Sanyo Chemical Industries) and the like. When blending an amphoteric surfactant into the oil-in-water emulsion cosmetic of the present invention, the blended amount thereof should be 0.01% to 1% by mass, and more preferably 0.05% to 0.5% by mass.

As mentioned above, the present invention provides an oil-in-water emulsion cosmetic that is premised on the use of an oil-soluble ultraviolet absorbing agent, so there is no need to blend a water-soluble ultraviolet absorbing agent into the present invention. However, it is possible to blend a water-soluble ultraviolet absorbing agent as an optional additive component as long as it is within a range not compromising the effects of the present invention.

The water-soluble ultraviolet absorbing agents that can be blended into the present invention are not particularly limited, and examples include phenylbenzimidazole sulfonic acid, 2-hydroxy-4-methoxybenzophenone sulfonic acid and the like.

The oil-in-water emulsion cosmetic of the present invention may be manufactured by means of generally known emulsification techniques such as, for example, heating and mixing the constituent components, and using phase transfer emulsification or the like.

The form of the oil-in-water emulsion cosmetic of the present invention is not particularly limited, and for example, it can be favorably used as a sunscreen milky lotion or as a sunscreen cream. Additionally, it can be widely applied to various types of cosmetics requiring sunscreen effects, such as makeup products and hair-care products.

EXAMPLES

Hereinafter, the present invention will be explained in further detail by providing specific examples, but the present invention is not limited to the examples below. Additionally, the blended amounts in the following examples and the like are indicated in percentage by mass where not specially noted otherwise.

Oil-in-water emulsion cosmetics having the compositions indicated in the tables below were prepared in accordance with conventional methods and the properties thereof were evaluated in accordance with the methods described below. The agar was dissolved in water or an aqueous component, thereafter allowed to cool and solidify, then blended in the form of agar microgels. The agar was dissolved in the water or the aqueous component by appropriately mixing and heating, and the solidification (gelification) was performed by allowing the agar solution to rest after the dissolution until a temperature lower than the gelification temperature (solidification temperature) was reached.

<1. Viscosity>

A VDA-type viscometer (Shibaura System DIGITAL VISMETRON VDA) was used to take measurements under conditions of 25° C., Rotor No. 3, rotation speed 12 rpm, and one minute.

<2. Ultraviolet Protection Performance>

Cosmetics (samples) according to each example were dripped, at a rate of 2 mg/cm$^2$, onto measurement plates (S plates) (5×5 cm V-groove PMMA plates, SPFMASTER-PA01), applied by finger for 60 seconds, and dried for 15 minutes to form coating films. On the other hand, controls were uncoated.

The absorbances of the formed coating films were measured using a Hitachi U-3500 self-recording spectrophotometer. The absorbances (Abs) were computed by using the following formula, to determine absorbance integral values for radiated light having a wavelength of 280 to 400 nm.

$$Abs=-\log(T/To)$$

T: transmittance of sample, To: transmittance of uncoated plate

If the ultraviolet protection performance value (absorbance integral value) determined in this way is 95 or higher, then sufficiently high sunscreen effects (for example, SPF 50+) can be achieved.

<3. Stability (Rolling Test)>

Cylindrical containers were half-filled with samples, the samples were subjected to rolling motions at 45 rpm for 4 hours at room temperature by means of a rolling tester (manufactured by Nigorikawa Rika Kogyo), and the changes in the states of the samples were observed. This test was performed using both glass containers and resin containers.

[Evaluation Criteria]
A: No separation was observed in outer appearance, remained in a single layer.
B: Some oil rising was observed in outer appearance but returned to homogeneous state after stirring.
C: Separation was observed in outer appearance and did not become homogeneous even after stirring.

<4. Stability (Vortex Test)>

Resin containers filled with samples were mounted on a compact shaker (manufactured by IKA Japan), the samples were subjected to shaking motions at 2200 rpm at 0° C., and the changes in the states of the samples were observed.

[Evaluation Criteria]
A: No separation was observed in outer appearance, remained in a single layer.
B: Some oil rising was observed in outer appearance but returned to homogeneous state after stirring.
C: Separation was observed in outer appearance and did not become homogeneous even after stirring.

<5. Texture (Wateriness)>

Samples of the examples and comparative examples were actually used by ten expert panelists, and evaluated regarding wateriness.

[Evaluation Criteria]
A: 7 or more panelists evaluated the sample as being watery.
B: 4 to 6 panelists evaluated the sample as being watery.
C: 3 or fewer panelists evaluated the sample as being watery.

TABLE 1

|  | Ex. 1 | Comp. Ex. 1 |
|---|---|---|
| Water | bal | bal |
| Ethanol | 10.0 | 10.0 |
| 1,3-Butylene glycol | 5.0 | 5.0 |
| Glycerin | 5.0 | 5.0 |
| Agar | 0.1 | — |
| Lauryl betaine | 0.1 | 0.1 |
| PEG-60 hardened castor oil | 0.3 | 0.3 |
| Xanthan gum | 0.1 | 0.1 |
| (Acrylates/($C_{10-30}$) alkyl acrylate) crosspolymer | 0.1 | 0.1 |
| Carbomer | 0.01 | 0.01 |
| Potassium hydroxide | 0.05 | 0.05 |
| Polybutylene glycol | 1.0 | 1.0 |
| Diisopropyl sebacate | 5.0 | 5.0 |
| Behenyl alcohol | 0.1 | 0.1 |
| Batyl alcohol | 0.1 | 0.1 |

TABLE 1-continued

|  | Ex. 1 | Comp. Ex. 1 |
|---|---|---|
| Dextrin (palmitate/ethylhexanoate) | 0.5 | 0.5 |
| Cyclopentasiloxane | 3.0 | 3.0 |
| Oxybenzone-3 | 2.0 | 2.0 |
| Octocrylene | 1.5 | 1.5 |
| Ethylhexyl methoxycinnamate | 7.5 | 7.5 |
| bis-Ethylhexyloxyphenol methoxyphenyl triazine | 1.5 | 1.5 |
| Diethylaminohydroxybenzoyl hexyl benzoate | 2.0 | 2.0 |
| Silicic anhydride (oil absorption rate 120 ml/100 g) | 5.0 | 5.0 |
| Phenoxyethanol | s.a. | s.a. |
| EDTA-3Na | 0.02 | 0.02 |
| Viscosity (mPa · s) | 7550 | 4380 |
| Ultraviolet protection performance | 106.4 | 82.7 |
| Stability (glass rolling) | A | B |
| Stability (resin rolling) | A | B |
| Stability (vortex) | A | A |
| Texture (wateriness) | A | A |

As shown in Table 1, when no agar microgel was blended, sufficient effects were not obtained in terms of sunscreen effects and stability.

TABLE 2

|  | Ex. 2 | Ex. 3 | Ex. 4 | Ex. 5 | Comp. Ex. 2 | Comp. Ex. 3 |
|---|---|---|---|---|---|---|
| Water | bal | bal | bal | bal | bal | bal |
| Ethanol | 10.0 | 10.0 | 10.0 | 10.0 | 10.0 | 10.0 |
| Lauryl betaine | 0.1 | 0.1 | 0.1 | 0.1 | 0.1 | 0.1 |
| PEG-60 hardened castor oil | 0.3 | 0.3 | 0.3 | 0.3 | 0.3 | 0.3 |
| 1,3-Butylene glycol | 5.0 | 5.0 | 5.0 | 5.0 | 5.0 | 5.0 |
| Glycerin | 5.0 | 5.0 | 5.0 | 5.0 | 5.0 | 5.0 |
| Agar | 0.1 | 0.1 | 0.1 | 0.1 | 0.1 | 0.1 |
| Xanthan gum | 0.1 | 0.1 | 0.1 | 0.1 | 0.1 | 0.1 |
| (Acrylates/$C_{10-30}$) alkyl acrylate) crosspolymer | 0.1 | 0.1 | 0.1 | 0.1 | 0.1 | 0.1 |
| Carbomer | 0.01 | 0.01 | 0.01 | 0.01 | 0.01 | 0.01 |
| Potassium hydroxide | 0.05 | 0.05 | 0.05 | 0.05 | 0.05 | 0.05 |
| Polybutylene glycol | 1.0 | 1.0 | 1.0 | 1.0 | 1.0 | 1.0 |
| Diisopropyl sebacate | 5.0 | 5.0 | 5.0 | 5.0 | 5.0 | 5.0 |
| Behenyl alcohol | 0.1 | 0.1 | 0.1 | 0.1 | 0.1 | 0.1 |
| Batyl alcohol | 0.1 | 0.1 | 0.1 | 0.1 | 0.1 | 0.1 |
| Dextrin (palmitate/ethylhexanoate) | 0.5 | 0.5 | 0.5 | 0.5 | 0.5 | 0.5 |
| Cyclopentasiloxane | 3.0 | 3.0 | 3.0 | 3.0 | 3.0 | 3.0 |
| Oxybenzone-3 | 2.0 | 2.0 | 2.0 | 2.0 | 2.0 | 2.0 |
| Octocrylene | 1.5 | 1.5 | 1.5 | 1.5 | 1.5 | 1.5 |
| Ethylhexyl methoxycinnamate | 7.5 | 7.5 | 7.5 | 7.5 | 7.5 | 7.5 |
| bis-Ethylhexyloxyphenol methoxyphenyl triazine | 1.5 | 1.5 | 1.5 | 1.5 | 1.5 | 1.5 |
| Diethylaminohydroxybenzoyl hexyl benzoate | 2.0 | 2.0 | 2.0 | 2.0 | 2.0 | 2.0 |
| Talc | 5.0 | — | — | — | — | — |
| Methyl methacrylate (oil absorption rate 46.5 ml/100 g) | — | 5.0 | — | — | — | — |
| Cellulose acetate (oil absorption rate 70 ml/100 g) | — | — | 5.0 | — | — | — |
| Silicic anhydride (oil absorption rate 20 ml/100 g) | — | — | — | 5.0 | — | — |
| Polyurethane (no oil absorption) | — | — | — | — | 5.0 | — |
| Phenoxyethanol | s.a. | s.a. | s.a. | s.a. | s.a. | s.a. |
| EDTA-3Na | 0.02 | 0.02 | 0.02 | 0.02 | 0.02 | 0.02 |
| Viscosity (mPa · s) | 3420 | 3240 | 3680 | 4110 | 4220 | 2820 |
| Ultraviolet protection performance | 118.6 | 101.5 | 98.1 | 114.6 | 87.7 | 93.9 |
| Stability (glass rolling) | A | A | A | A | A | A |
| Stability (resin rolling) | A | A | A | A | A | A |
| Stability (vortex) | A | A | A | A | A | A |
| Texture (wateriness) | A | A | A | A | A | A |

As shown in Table 2, when talc or a highly oil-absorbent spherical powder having an oil absorption rate of 20 ml/100 g or higher was used as the powder, high sunscreen effects were obtained, low viscosity and stability were obtained, and the texture was excellent. In contrast therewith, when a lowly oil-absorbent spherical powder having an oil absorption rate of less than 20 ml/100 g was blended, or these powders were not included, the sunscreen effects were poor.

TABLE 3

|  | Comp. Ex. 4 | Comp. Ex. 5 | Comp. Ex. 6 |
|---|---|---|---|
| Water | bal | bal | bal |
| Ethanol | 10.0 | 10.0 | 10.0 |
| 1,3-Butylene glycol | 5.0 | 5.0 | 5.0 |
| Glycerin | 5.0 | 5.0 | 5.0 |
| Agar | 0.1 | 0.1 | 0.1 |
| Lauryl betaine | 0.1 | 0.1 | 0.1 |
| PEG-10 dimethicone | 0.3 | — | — |
| Potassium cetyl phosphate | — | 0.3 | — |
| Xanthan gum | 0.1 | 0.1 | 0.1 |
| (Acrylates/$C_{10-30}$) alkyl acrylate) crosspolymer | 0.1 | 0.1 | 0.1 |
| Carbomer | 0.01 | 0.01 | 0.01 |
| Potassium hydroxide | 0.05 | 0.05 | 0.05 |
| Polybutylene glycol | 1.0 | 1.0 | 1.0 |

TABLE 3-continued

|  | Comp. Ex. 4 | Comp. Ex. 5 | Comp. Ex. 6 |
|---|---|---|---|
| Diisopropyl sebacate | 5.0 | 5.0 | 5.0 |
| Behenyl alcohol | 0.1 | 0.1 | 0.1 |
| Batyl alcohol | 0.1 | 0.1 | 0.1 |
| Dextrin (palmitate/ethylhexanoate) | 0.5 | 0.5 | 0.5 |
| Cyclopentasiloxane | 3.0 | 3.0 | 3.0 |
| Oxybenzone-3 | 2.0 | 2.0 | 2.0 |
| Octocrylene | 1.5 | 1.5 | 1.5 |
| Ethylhexyl methoxycinnamate | 7.5 | 7.5 | 7.5 |
| bis-Ethylhexyloxyphenol methoxyphenyl triazine | 1.5 | 1.5 | 1.5 |
| Diethylaminohydroxybenzoyl hexyl benzoate | 2.0 | 2.0 | 2.0 |
| Silicic anhydride (oil absorption rate 120 ml/100 g) | 5.0 | 5.0 | 5.0 |
| Phenoxyethanol | s.a. | s.a. | s.a. |
| EDTA-3Na | 0.02 | 0.02 | 0.02 |
| Viscosity (mPa · s) | 7500 | 4430 | 4380 |
| Ultraviolet protection performance | 101.0 | 57.3 | 104.7 |
| Stability (glass rolling) | C | C | A |
| Stability (resin rolling) | C | C | C |
| Stability (vortex) | A | C | A |
| Texture (wateriness) | A | C | A |

As shown in Table 3, when surfactants other than polyoxyethylene-hardened castor oil were used, the preparation stability was poor.

TABLE 4

|  | Comp. Ex. 7 | Comp. Ex. 8 | Comp. Ex. 9 | Comp. Ex. 10 |
|---|---|---|---|---|
| Water | bal | bal | bal | bal |
| Ethanol | 10.0 | 10.0 | 10.0 | 10.0 |
| 1,3-Butylene glycol | 5.0 | 5.0 | 5.0 | 5.0 |
| Glycerin | 5.0 | 5.0 | 5.0 | 5.0 |
| Agar | 0.1 | 0.1 | 0.1 | 0.1 |
| Lauryl betaine | 0.1 | 0.1 | 0.1 | 0.1 |
| PEG-60 hardened castor oil | 0.3 | 0.3 | 0.3 | 0.3 |
| Xanthan gum | 0.1 | 0.1 | 0.1 | 0.1 |
| (Acrylates/$C_{10-30}$) alkyl acrylate) crosspolymer | — | — | — | 0.15 |
| Stearoxyhydroxypropyl methyl cellulose | 0.1 | — | — | — |
| Methyl methacrylate/butyl methacrylate/ methoxypolyethylene glycol monomethacrylate/ethylene glycol dimethacrylate copolymer | — | 0.1 | — | — |
| Carbomer | 0.01 | 0.01 | 0.01 | 0.01 |
| Potassium hydroxide | 0.05 | 0.05 | 0.05 | 0.05 |
| Polybutylene glycol | 1.0 | 1.0 | 1.0 | 1.0 |
| Diisopropyl sebacate | 5.0 | 5.0 | 5.0 | 5.0 |
| Behenyl alcohol | 0.1 | 0.1 | 0.1 | 0.1 |
| Batyl alcohol | 0.1 | 0.1 | 0.1 | 0.1 |
| Dextrin (palmitate/ethylhexanoate) | 0.5 | 0.5 | 0.5 | 0.5 |
| Cyclopentasiloxane | 3.0 | 3.0 | 3.0 | 3.0 |
| Oxybenzone-3 | 2.0 | 2.0 | 2.0 | 2.0 |
| Octocrylene | 1.5 | 1.5 | 1.5 | 1.5 |
| Ethylhexyl methoxycinnamate | 7.5 | 7.5 | 7.5 | 7.5 |
| bis-Ethylhexyloxyphenol methoxyphenyl triazine | 1.5 | 1.5 | 1.5 | 1.5 |
| Diethylaminohydroxybenzoyl hexyl benzoate | 2.0 | 2.0 | 2.0 | 2.0 |
| Silicic anhydride (oil absorption rate 120 ml/100 g) | 5.0 | 5.0 | 5.0 | 5.0 |
| Phenoxyethanol | s.a. | s.a. | s.a. | s.a. |
| EDTA-3Na | 0.02 | 0.02 | 0.02 | 0.02 |
| Viscosity (mPa · s) | 2140 | 2360 | 7660 | 9840 |
| Ultraviolet protection performance | 104.0 | 106.3 | 118.2 | 107.9 |
| Stability (glass rolling) | C | C | B | A |
| Stability (resin rolling) | C | C | B | A |
| Stability (vortex) | A | C | C | B |
| Texture (wateriness) | C | C | A | C |

As shown in Table 4, when a polymer other than an (acrylates/($C_{10-30}$) alkyl acrylate) crosspolymer was used as the emulsifier, the stability was poor. Additionally, the texture was poor when the amount of the (acrylates/($C_{10-30}$) alkyl acrylate) crosspolymer was too high.

The invention claimed is:

1. An oil-in-water emulsion cosmetic, having a viscosity, at 25° C., of 10000 mPa·s or lower, comprising:
    (A) an agar microgel;
    (B) one or more powders selected from among (b1) clay mineral powders and (b2) highly oil-absorbent spherical powders;
    (C) a polyoxyethylene-hardened castor oil having an HLB value of 10 to 17;
    (D) an oil-soluble ultraviolet absorbing agent;
    (E) 0.01% to 0.13% by mass of an (acrylates/($C_{10-30}$) alkyl acrylate) crosspolymer; and
    (F) 0% to 0.5% by mass of an ultraviolet scattering agent.

2. The oil-in-water emulsion cosmetic, as in claim 1, further comprising:
    an oil-phase thickener; and
    wherein the oil-phase thickener is a dextrin fatty acid ester.

3. The oil-in-water emulsion cosmetic, as in claim 1, further comprising:
    a carboxyvinyl polymer.

4. The oil-in-water emulsion cosmetic, as in claim 1, further comprising:
    a humectant.

* * * * *